United States Patent
Shaw et al.

(10) Patent No.: US 9,931,475 B2
(45) Date of Patent: *Apr. 3, 2018

(54) FRONTAL ATTACHMENT DEVICE FOR SYRINGE WITH PINCH-ACTIVATED NEEDLE RETRACTION

(71) Applicant: Retractable Technologies, Inc., Little Elm, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,989

(22) Filed: Jul. 5, 2016

(65) Prior Publication Data

US 2016/0310677 A1    Oct. 27, 2016

Related U.S. Application Data

(63) Continuation of application No. 13/842,000, filed on Mar. 15, 2013, now Pat. No. 9,381,309, which is a
(Continued)

(51) Int. Cl.
*A61M 5/32* (2006.01)
*A61M 5/34* (2006.01)

(52) U.S. Cl.
CPC .......... *A61M 5/3232* (2013.01); *A61M 5/345* (2013.01); *A61M 2005/3227* (2013.01); *A61M 2005/3236* (2013.01)

(58) Field of Classification Search
CPC .. A61M 2005/3227; A61M 2005/3236; A61M 5/3232; A61M 5/345
See application file for complete search history.

(56) References Cited

U.S. PATENT DOCUMENTS

| 4,466,446 A | 8/1984 | Baidwan et al. |
| 4,747,831 A | 5/1988 | Kulli |

(Continued)

FOREIGN PATENT DOCUMENTS

| EP | 0479303 | 8/1992 |
| EP | 1161962 | 12/2001 |

*Primary Examiner* — Imani Hayman
(74) *Attorney, Agent, or Firm* — Ross Barnes LLP; Monty L. Ross; Robin L. Barnes (57) ABSTRACT

A retractable needle device attachable to the front of a fluid collection or infusion device such as a syringe, the retractable needle device comprising a housing having an engagement member, a slide support surface, a retraction cavity and a first pinch surface; a needle; a needle alignment member comprising a needle tube and a second pinch surface; and a needle retraction mechanism positioned within the needle tube and configured to bias the needle rearwardly; wherein the first and second pinch surfaces are configured so that a pinching force applied to them will cause relative lateral movement between the housing and needle alignment member. This translational movement from an injection position, wherein the needle is aligned with the syringe connector, to a retraction position, wherein the needle is aligned with the retraction cavity, allows the needle retraction mechanism to force the needle into the retraction cavity.

3 Claims, 8 Drawing Sheets

Related U.S. Application Data continuation-in-part of application No. 13/470,855, filed on May 14, 2012, now Pat. No. 8,469,927, which is a continuation of application No. 12/136,462, filed on Jun. 10, 2008, said application No. 13/842,000 is a continuation-in-part of application No. 13/714,819, filed on Dec. 14, 2012, now Pat. No. 9,138,545.

(56) References Cited

U.S. PATENT DOCUMENTS

| | | |
|---|---|---|
| 4,813,426 A | 3/1989 | Haber et al. |
| 4,941,883 A | 7/1990 | Venturini |
| 4,973,316 A | 11/1990 | Dysarz |
| 5,163,916 A | 11/1992 | Sunderland |
| 5,263,942 A | 11/1993 | Smedley et al. |
| 5,298,023 A | 3/1994 | Haber |
| 5,370,628 A | 12/1994 | Allison et al. |
| 5,395,337 A | 3/1995 | Clemens et al. |
| 5,423,758 A | 6/1995 | Shaw |
| 5,445,618 A | 8/1995 | Adobbati |
| 5,503,010 A | 4/1996 | Yamanaka |
| 5,573,510 A | 12/1996 | Isaacson |
| 5,685,863 A | 11/1997 | Botich et al. |
| 5,704,920 A | 1/1998 | Gyure |
| 5,728,073 A | 3/1998 | Whisson |
| 5,779,679 A | 7/1998 | Shaw |
| 5,795,339 A | 8/1998 | Erskine |
| 5,957,887 A | 9/1999 | Osterlind et al. |
| 5,964,731 A | 10/1999 | Kovelman |
| 6,039,713 A | 3/2000 | Botich et al. |
| 6,063,040 A | 5/2000 | Owen et al. |
| 6,210,371 B1 | 4/2001 | Shaw |
| 6,277,102 B1 | 8/2001 | Carilli |
| 6,468,250 B2 | 10/2002 | Yang |
| 6,794,423 B1 | 9/2004 | Li |
| 6,808,512 B1 | 10/2004 | Lin et al. |
| 7,351,224 B1 | 4/2008 | Shaw |
| 8,292,852 B2 | 10/2012 | Mulholland |
| 8,343,094 B2 | 1/2013 | Shaw |
| 2001/0021827 A1 | 9/2001 | Ferguson et al. |
| 2002/0068907 A1 | 6/2002 | Dysarz |
| 2002/0082560 A1 | 6/2002 | Yang |
| 2003/0078540 A1 | 4/2003 | Saulenas et al. |
| 2003/0171695 A1 | 9/2003 | Zurcher |
| 2003/0181871 A1 | 9/2003 | Wilkinson et al. |
| 2003/0236504 A1 | 12/2003 | Chen |
| 2004/0015135 A1 | 1/2004 | Wilkinson |
| 2004/0019329 A1 | 1/2004 | Erskine |
| 2004/0133172 A1 | 7/2004 | Wilkinson |
| 2004/0204688 A1 | 10/2004 | Lin et al. |
| 2005/0004524 A1 | 1/2005 | Newby et al. |
| 2005/0288607 A1 | 12/2005 | Konrad |
| 2006/0155244 A1 | 7/2006 | Popov |
| 2006/0189934 A1 | 8/2006 | Kuracina et al. |
| 2006/0235354 A1 | 10/2006 | Kaal et al. |
| 2007/0260189 A1 | 11/2007 | Shaw et al. |
| 2007/0293826 A1 * | 12/2007 | Wall .............. A61M 5/19 604/200 |
| 2008/0132851 A1 | 6/2008 | Shaw et al. |
| 2008/0132854 A1 | 6/2008 | Sharp |
| 2008/0287881 A1 | 11/2008 | Kiehne |
| 2008/0319345 A1 | 12/2008 | Swenson |
| 2009/0198196 A1 | 8/2009 | West et al. |
| 2009/0306601 A1 | 12/2009 | Shaw et al. |
| 2010/0000040 A1 | 1/2010 | Shaw et al. |
| 2010/0003067 A1 | 1/2010 | Shaw et al. |
| 2010/0241029 A1 | 9/2010 | Mahurkar |
| 2010/0286604 A1 | 11/2010 | Shaw |
| 2011/0264037 A1 | 10/2011 | Foshee et al. |
| 2012/0022464 A1 | 1/2012 | Zivkovic et al. |
| 2012/0071790 A1 | 3/2012 | Mahurkar |
| 2012/0071827 A1 | 3/2012 | Zivkovic et al. |
| 2012/0078225 A1 | 3/2012 | Zivkovic et al. |
| 2012/0259243 A1 | 10/2012 | Shaw et al. |
| 2012/0316466 A1 | 12/2012 | Crawford et al. |

* cited by examiner

FRONTAL ATTACHMENT DEVICE FOR SYRINGE WITH PINCH-ACTIVATED NEEDLE RETRACTION

CROSS-REFERENCE TO RELATED APPLICATIONS

This application is a continuation-in-part of U.S. patent application Ser. No. 13/470,855, filed May 14, 2012, which is a continuation of U.S. patent application Ser. No. 12/136,462, filed Jun. 10, 2008, and the portions of those applications that relate to the embodiments of FIGS. 4 and 5 as disclosed therein are incorporated by reference into this application. This application is also a continuation-in part of U.S. patent application Ser. No. 13/714,819, filed Dec. 14, 2012.

BACKGROUND OF THE INVENTION

1. Field of the Invention

This invention relates to a newly disclosed frontal attachment having a retractable needle that is attachable to conventional medical devices such as syringes. The invention relates more particularly to a medical device comprising in combination a needle, needle positioner, needle retraction mechanism, and a syringe engaging member with a retraction tube. The subject device has a needle retraction mechanism that is activated by pinching action and retracts the needle from a patient and propels it into a retraction tube that is part of the hub assembly.

2. Description of Related Art

Conventional syringes comprising a generally cylindrical barrel, a fixed needle projecting forwardly from the barrel, and a plunger slidably disposed inside the barrel through an opening in the rear of the barrel are well known. More recently, syringes have been made with a luer connector on the front of the barrel to which a needle hub is attachable to allow needles of different gauges or sizes to be used with a commonly configured barrel.

Even more recently, in an effort to control the spread of blood-borne pathogens and the incidence of contamination by contact with either exposed needles or bodily fluids, syringes having fixed or changeable needles have been designed to embody various "safety" elements. Such "safety" elements should desirably include a retractable needle, but many products marketed as having "safety" elements include, for example, covers or guards that are manually operated by medical personnel administering an injection to shield or cover the needle tip following removal of the needle from a patient.

Some previously disclosed needle retraction systems without changeable needles are activated either manually or automatically by application of a force upon completion of an injection to force the needle and needle tip back inside a retraction chamber. The only known syringe having a changeable, retractable needle does not have a conventional luer lock connection, and the retraction mechanism is activated by the application of a forwardly directed force to the plunger handle following removal of the needle from a patient, thereby exposing the needle and also exposing the user to the risk of needle-stick injury.

Although many advancements in syringe technology have been made in recent years, a frontal attachment device is needed that can be used with a standard syringe having a conventional luer lock connector, that offers the advantages of a changeable needle in combination with the advantages of a retractable needle providing sufficient retraction force to retract the needle while inserted into a patient, and that can be activated simply and easily by the application of a pinching force.

SUMMARY OF THE INVENTION

A medical device is disclosed that features automated needle retraction wherein needle retraction is initiated by the application of opposed compressive forces in line with a principal sliding interface to reduce the likelihood of sticking, hang-up or canting that could otherwise impede the translational movement of one element of the device relative to another. As applied to a syringe, the subject medical device further includes an automated retraction device wherein the needle retraction mechanism can be activated independently of the position of the plunger.

A retractable needle device is disclosed that comprises an engagement member selectively attachable to a cooperatively configured, forwardly facing portion of a medical device such as a conventional syringe having a forwardly facing luer lock connector. Other medical devices with which the retractable needle device can be used can include, for example and without limitation, other fluid collection or infusion devices that can utilize a retractable needle. In addition to the engagement member, the retractable needle device desirably comprises a retraction tube, a needle alignment member comprising a needle tube, a rearwardly-biased needle retraction mechanism seated inside the needle tube, a retractable needle projecting forwardly of the needle alignment member, and a fluid flow path from the fluid chamber through the engagement member, needle tube, needle retraction mechanism and needle, wherein the needle is retracted following use into the retraction tube applying a pinching force. As used throughout this disclosure, the terms "attachable," "detachable" and "changeable" are generally used to characterize frontal attachments, such as needles or needle/hub combinations, that are selectively attachable to, detachable from, or otherwise changeable in relation to a medical device such as a syringe for purposes such as, without limitation, selecting a particular gauge needle for a particular clinical use.

If desired, a retractable needle device as disclosed here can also be made with a slip-fit luer cone, snap-on or other attachment mechanism instead of a conventional luer lock connector provided that the medical device with which it is used is cooperatively configured. A retractable needle device as disclosed here desirably comprises a needle that is retractable, and retraction is activated by pinching pressure applied generally perpendicularly to the longitudinal axis through the needle. A satisfactory retractable needle device as disclosed here desirably has sufficient retraction force to retract a needle that is still inserted into a patient's body and thereby prevents exposure of the contaminated needle to others. A retractable needle device as disclosed here desirably utilizes a retraction tube that is not embodied, for example, in a syringe barrel or plunger handle, and is instead part of an attachable assembly.

Following an injection using a medical device provided with the medical device disclosed here, a clinician administering the injection desirably applies digital pressure to two opposed textured tabs with a thumb and a finger. Application of pinching pressure causes relative motion of the needle holder and needle away from the syringe connector and toward the retraction tube. This relative motion is continued until the needle holder is aligned with a forwardly facing opening of the retraction tube, at which point the needle retraction mechanism propels the needle holder into the retraction tube. The needle holder carries the attached needle rearwardly to a fully retracted position where the needle is released from the patient and the needle tip no longer projects forwardly from the needle tube. Also, using the device disclosed here, if a clinician administering an injection needs or decides to terminate the injection, the needle can be retracted to prior to infusing all the fluid in a syringe.

BRIEF DESCRIPTION OF THE DRAWINGS

The apparatus of the invention is further described and explained in relation to the following drawings wherein.

Like reference numerals are used to describe like features in all Figures of the drawings.

DESCRIPTION OF THE PREFERRED EMBODIMENTS

For illustrative purposes, the retractable needle device of the invention is described below in relation to a medical device that is a syringe assembly onto which a retractable needle device of the invention has been releasably installed. It should be appreciated, however, that the retractable needle device of the invention is similarly useful for collecting or infusing fluids with other medical devices that are not syringes.

Figure 1:
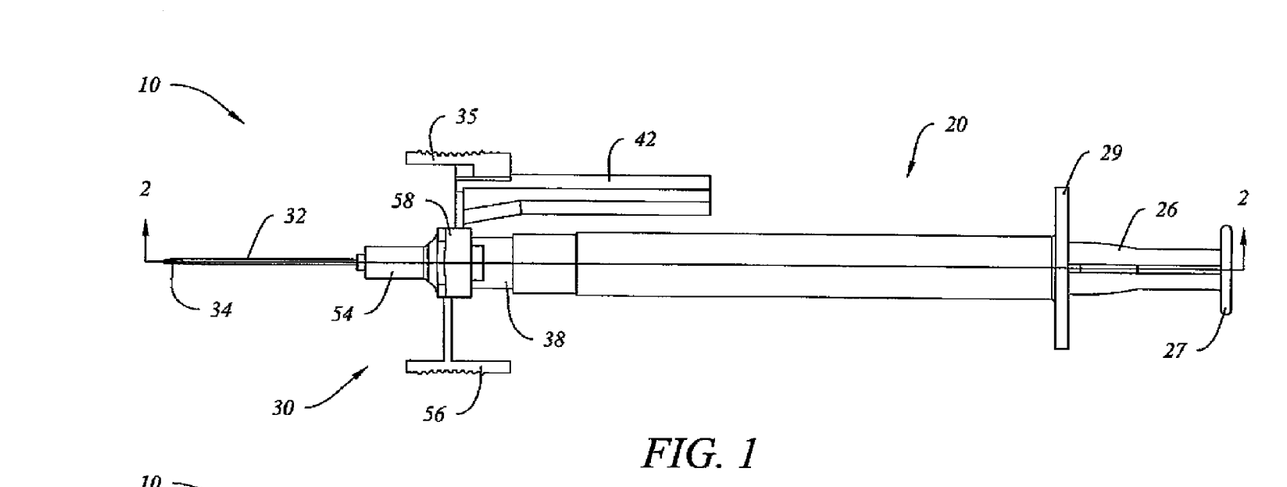
FIG. 1 is a side elevation view of one embodiment of a syringe with an attached retractable needle device.
Figure 2:
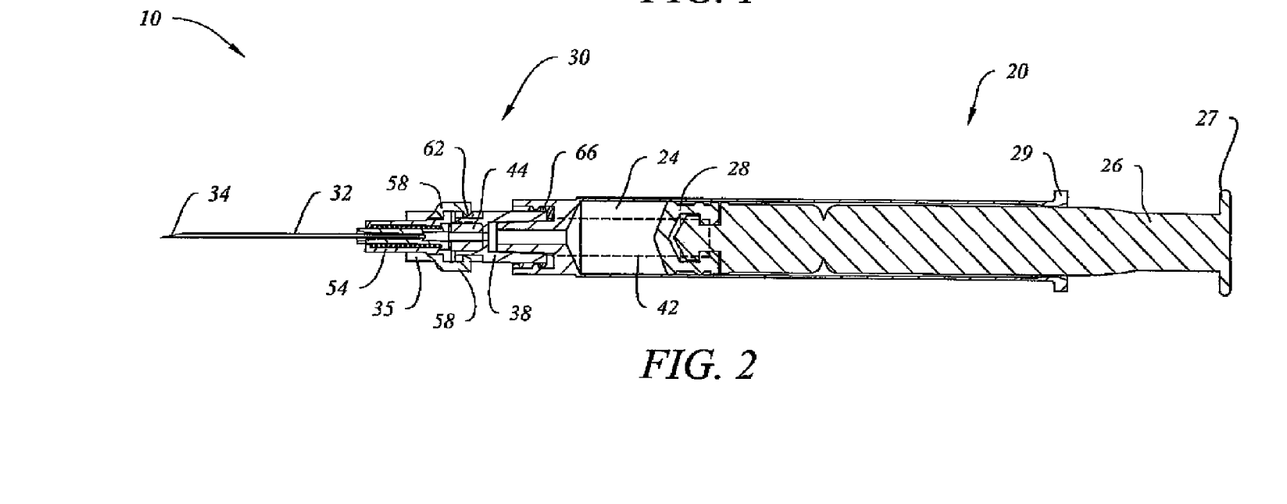
FIG. 2 is a cross-sectional view of the apparatus of FIG. 1 taken along line 2-2 of FIG. 1.
Figure 4:
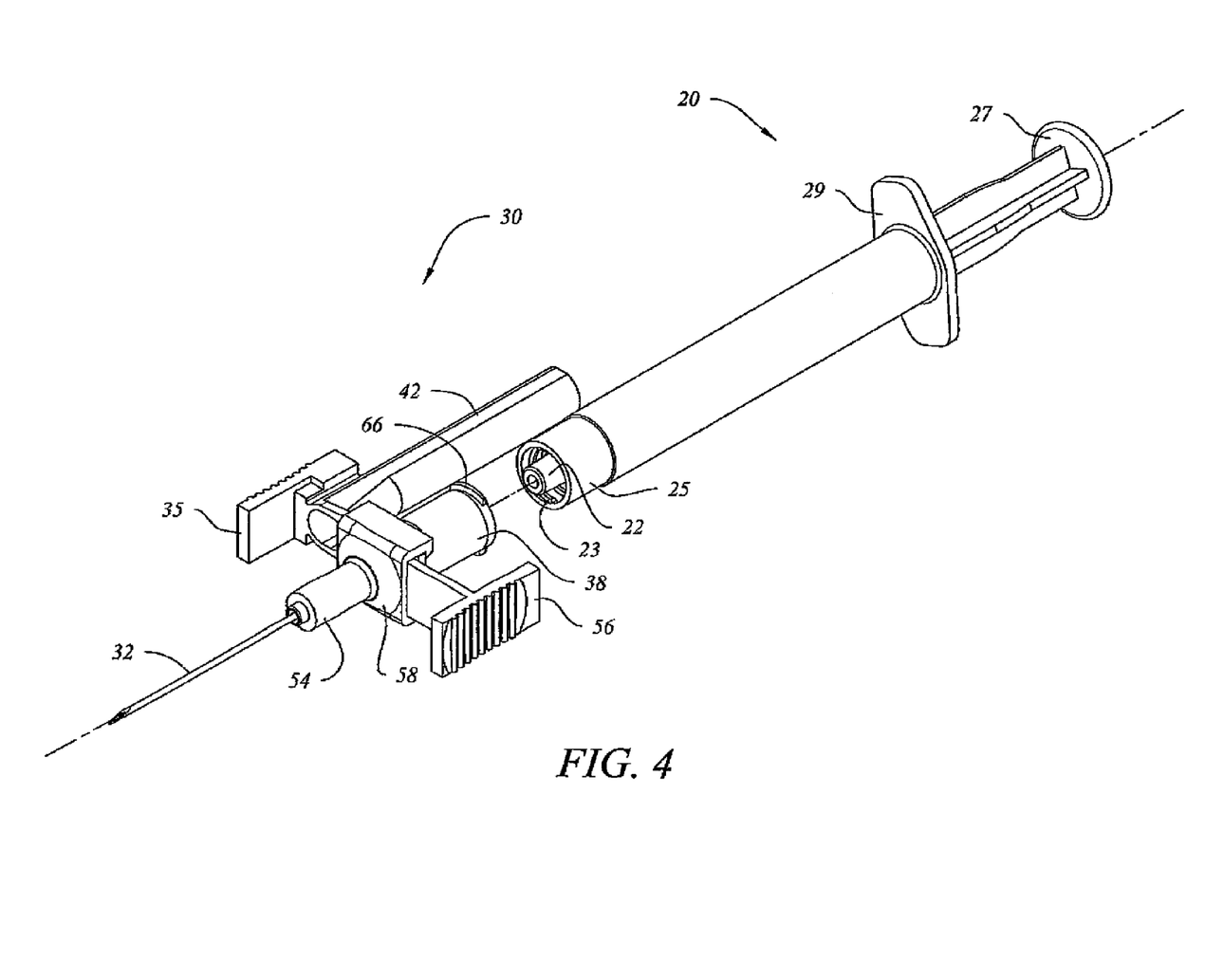
FIG. 4 is a perspective view illustrating cooperation of a syringe connector of a retractable needle device with a luer lock connection of a syringe barrel.

FIGS. 1, 2 and 4 depict a syringe assembly 10 comprising syringe barrel 20, having a luer lock connector 22, 23 disposed at the front end and a plunger handle 26 with plunger seal 28 slidably engaging the inside wall of syringe barrel 20, and a retractable needle device 30 attached to War lock connector 22, 23 so as to establish fluid communication between fluid chamber 24 of syringe barrel 20 and needle 32 of retractable needle device 30. Plunger handle 26 extends rearwardly from an opening in the back of syringe barrel 20 and is shown positioned as it could be prior to the injection of a fluid disposed inside fluid chamber 24 into a patient (not shown) if tip 34 of needle 32 were inserted into the patient, recognizing that the position of plunger seal 28 relative to syringe barrel 20 will depend upon the amount of fluid that is drawn into fluid chamber 24. An injection force is applied to a fluid disposed inside fluid chamber 24 through plunger handle 26 by depressing thumb cap 27 of plunger handle 26 while stabilizing syringe barrel 20 by applying oppositely directed finger farce to the forwardly facing surfaces of outwardly projecting flanges 29.

Figure 3:
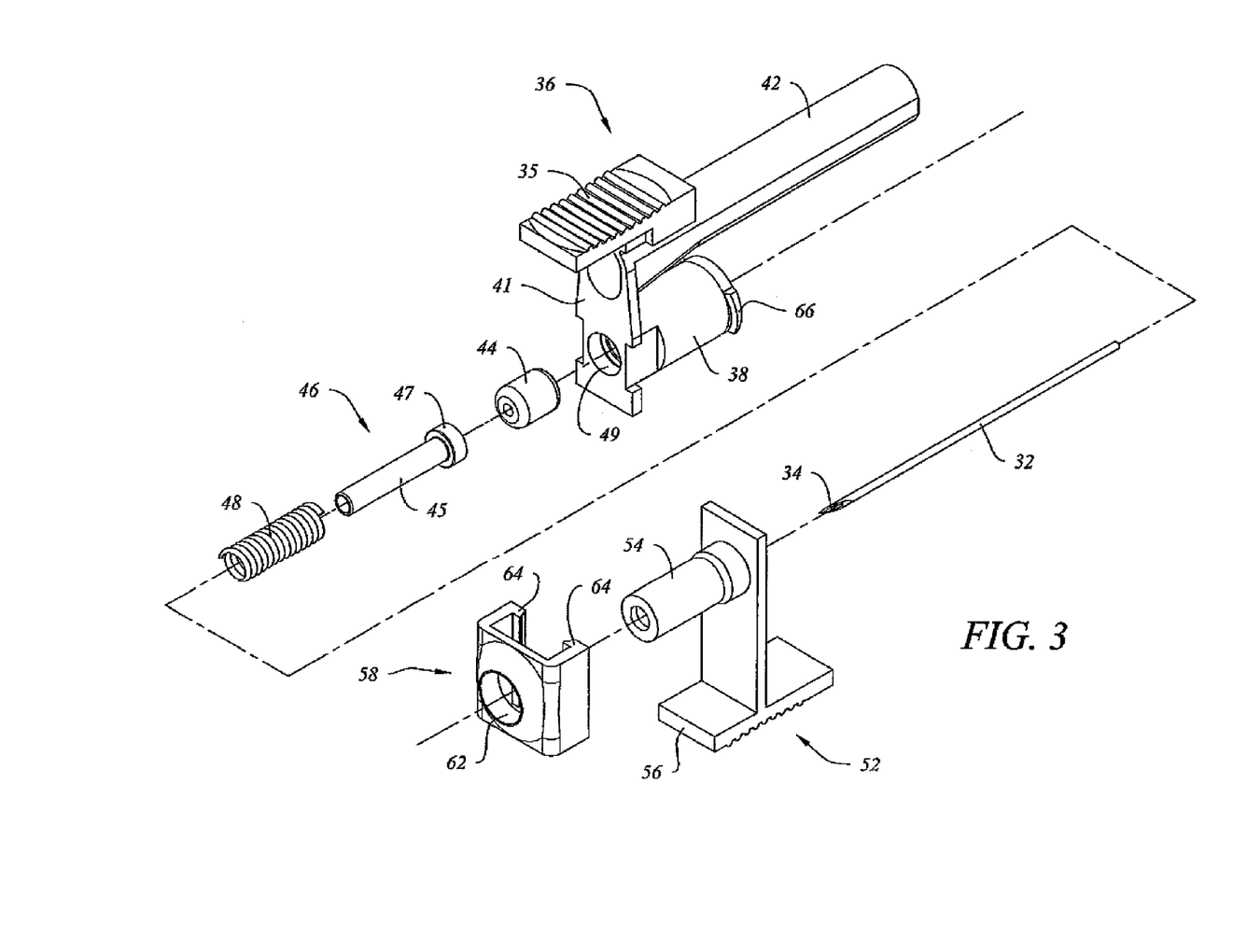
FIG. 3 is an exploded view of the retractable needle device of FIG. 1.

FIG. 3 is an exploded view of retractable needle device 30 further illustrating its components. Housing 36 preferably comprises first pinch tab 35, connector tube 38, slide support surface 41, and retraction tube 42. Connector tube 38 is desirably configured to form a fluid tight seal between luer lock connector 22 of syringe barrel 20 and needle holder 46. Fluid seal 44 desirably comprises an elastomeric material and at least a portion of fluid seal 44 is positioned within an annular recess 49 defined in forwardly facing slide support surface 41. Fluid seal 44 provides a fluid seal between housing 36 or luer tip 22 and needle holder 46. First pinch tab 35 preferably comprises ridges or other texture to provide slip resistance when gripped with a finger or thumb.

Forward of fluid seal 44 is needle holder 46, which is attached to needle 32. Needle holder 46 comprises an axial bore through a generally cylindrical elongate body 45 and larger diameter head 47. Body 45 is preferably slightly longer than needle tube 54. Retraction spring 48 is positioned around body 45 and is compressed between an annular ledge inside the front end of needle tube 54 and a forwardly facing annular shoulder between body 45 and head 47. Prior to needle retraction, retraction spring 48 is under compression and biases needle holder 46 and needle 32 rearwardly relative to needle tube 54 and housing 36.

Retractable needle device 30 also comprises needle alignment member 52. Needle alignment member 52 comprises a rearwardly facing surface that slidably engages forwardly facing sliding surface 41 of housing 36, and further comprises forwardly projecting needle tube 54 and second pinch tab 56. Second pinch tab 56 is desirably positioned on an opposing side of syringe barrel 20 from first pinch tab 35. Second pinch tab 56 is preferably textured similarly to first pinch tab 35. A retainer clip 58 comprises a hole 62 configured to engage needle tube 54. Retainer clip 58 also comprises retaining brackets 64 configured to retain needle alignment member 52 against housing 36, while allowing sliding motion between them when a sufficient pinching force is applied to first and second pinch tabs 35, 56.

As shown in FIG. 4, tapered luer cone member 22 comprising a substantially cylindrical bore cooperates with annular collar 25 having internal threads 23 disposed in spaced-apart relation to tapered luer cone member 22 to form a luer lock connector that is engageable with locking wedges 66 of housing 36 to provide a fluid-tight seal between housing 36 and syringe barrel 20 whenever needle tube 54 is coaxially aligned with barrel 20. When syringe assembly 10 is assembled as shown in FIG. 1, a continuous fluid flow path is formed from fluid chamber 24 (FIG. 2) through housing 36, fluid seal 44 and needle holder 46 to needle 32.

Figure 5:
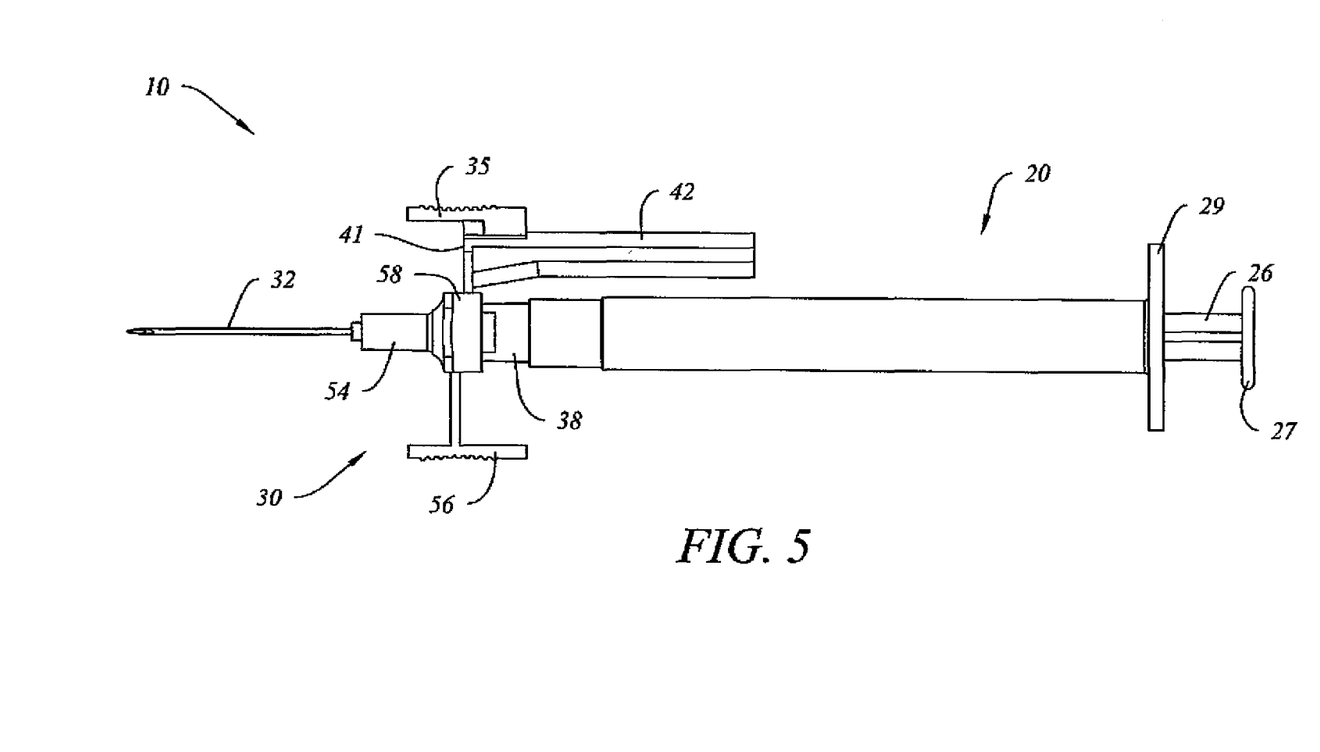
FIG. 5 shows the syringe and retractable needle device of FIG. 1 after syringe plunger has been fully depressed.
Figure 6:
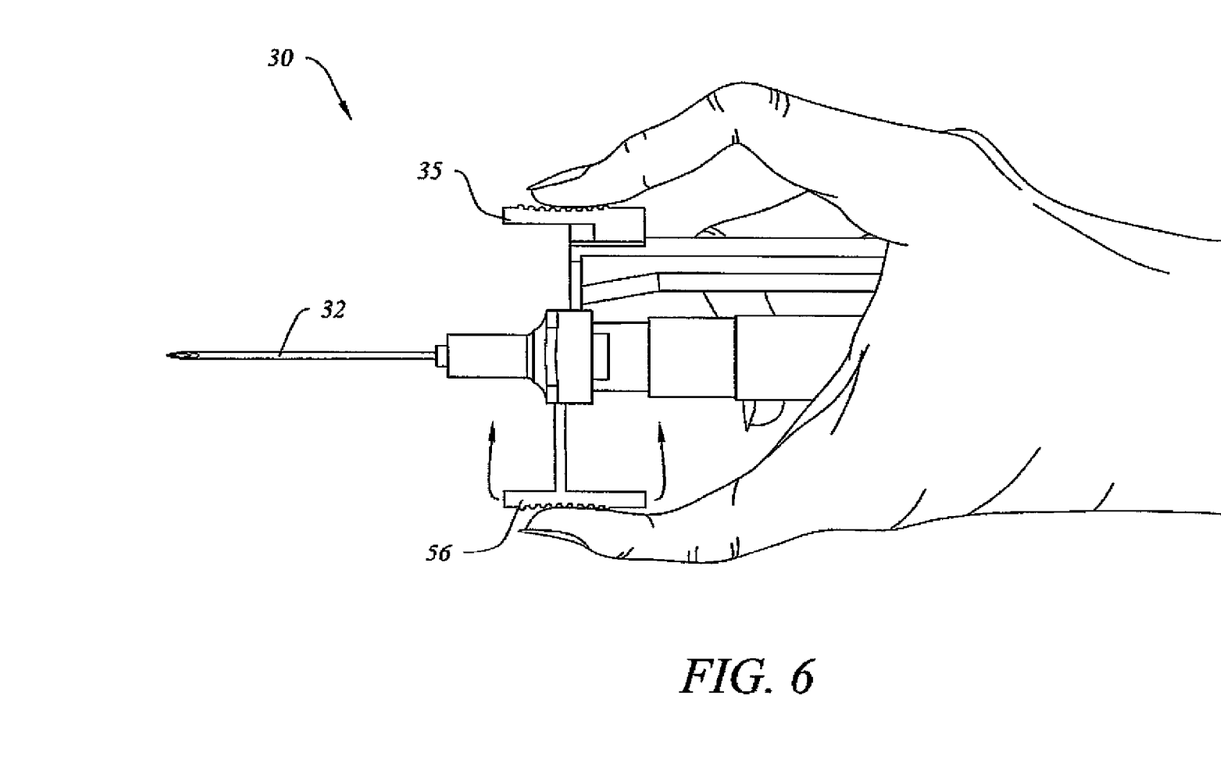
FIG. 6 is a perspective view of a retractable needle device being activated by a user.

Operation of the syringe assembly 10 during filling and injection is similar to many existing syringe and needle systems and will be readily understood by those of ordinary skill in the art. Referring to FIG. 5, syringe assembly 10 is shown with plunger handle 26 advanced relative to syringe barrel 20 to the point it will be following an injection, when plunger seal 28 has forced the fluid out of fluid chamber 24. This is the position in which plunger handle 26 will desirably remain relative to syringe barrel 20 during activation of the retractable needle device 30. Following an injection, the clinician administering the injection can retract needle 32 by pinching first pinch tab 35 toward second pinch tab 56, as illustrated in FIG. 6.

Figure 7:
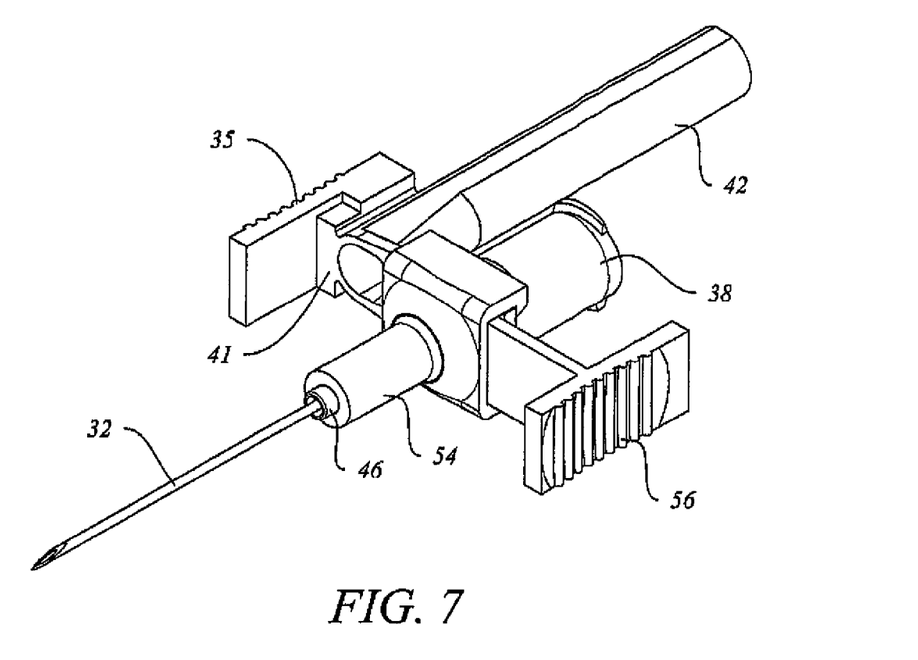
FIG. 7 is a perspective view of a retractable needle device prior to retraction of the needle.
Figure 8:
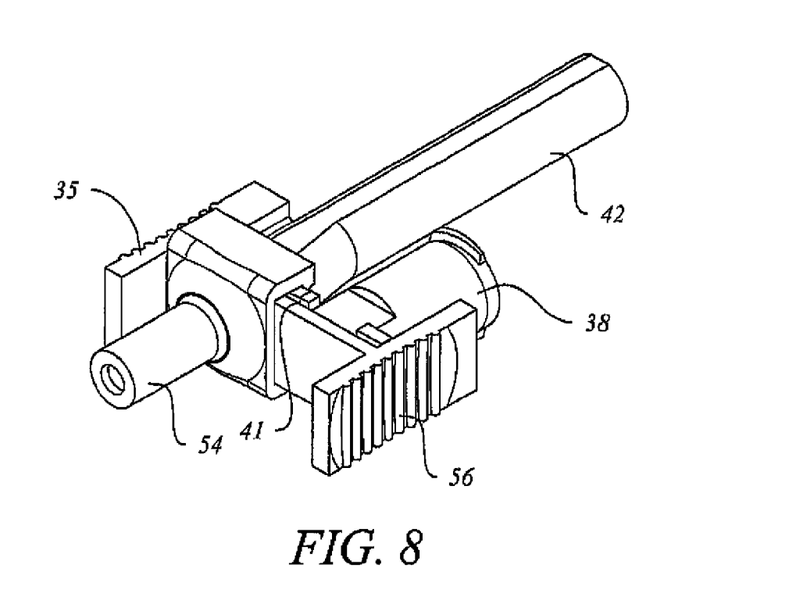
FIG. 8 is a perspective view of a retractable needle device after retraction of the needle.
Figure 9:
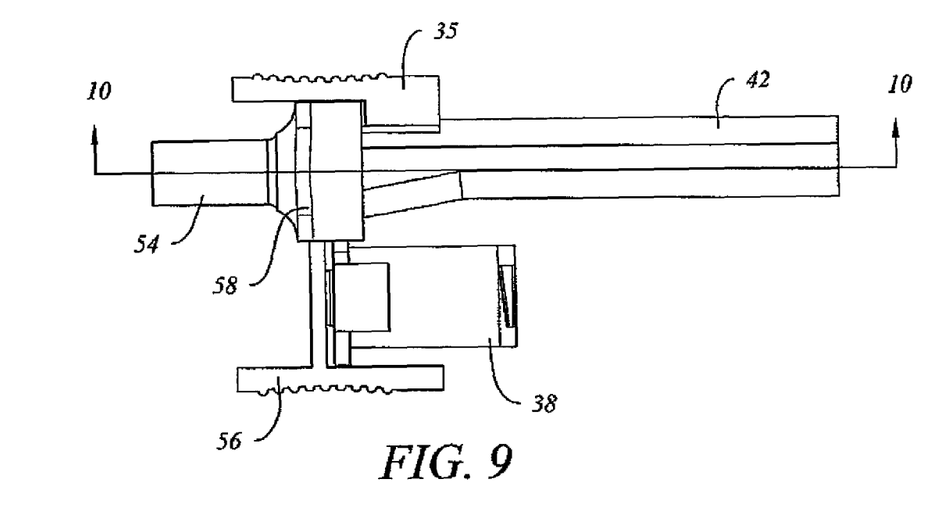
FIG. 9 is an elevation view of the retractable needle device of FIG. 8.
Figure 10:
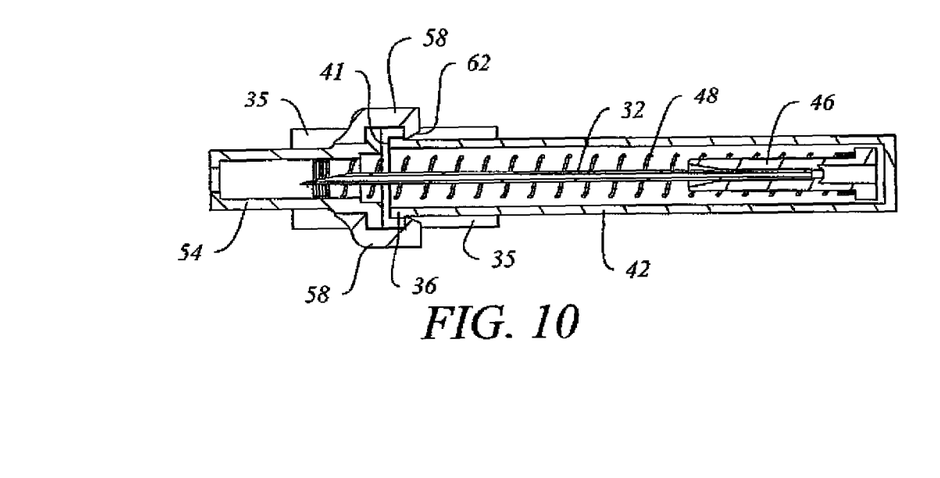
FIG. 10 is a cross-section view of the retractable needle device of FIG. 9 taken along line 10-10.

FIGS. 7 and 8 illustrate an assembled retractable needle device 30 before (FIG. 7) and after (FIG. 8) needle 32 has retracted. In FIG. 7 a forward end of needle holder 46 protrudes slightly beyond the front end of needle tube 54. In FIG. 8, needle 32 and needle holder 46 have been retracted into retraction tube 42 and are no longer visible. FIG. 9 is an elevation view of the retractable needle device 30, in retracted position, of FIG. 8. FIG. 10 is cross-section view of the same retractable needle device 30, illustrating the arrangement of needle 32 and needle holder 46 after retraction of needle 32.

Figure 11:
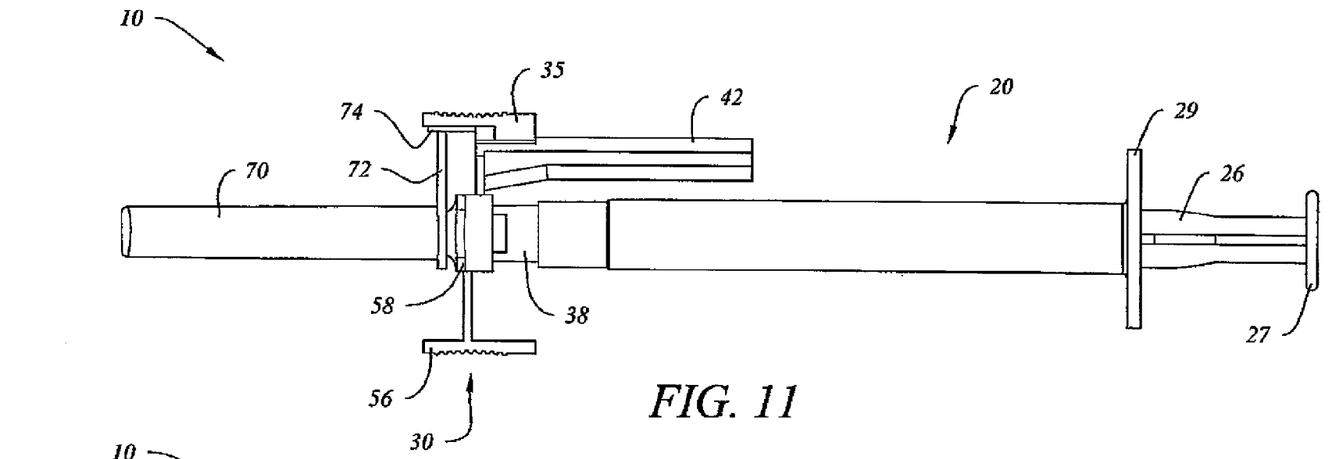
FIG. 11 is an elevation view of the device as in FIG. 1 with a needle cover installed.
Figure 12:
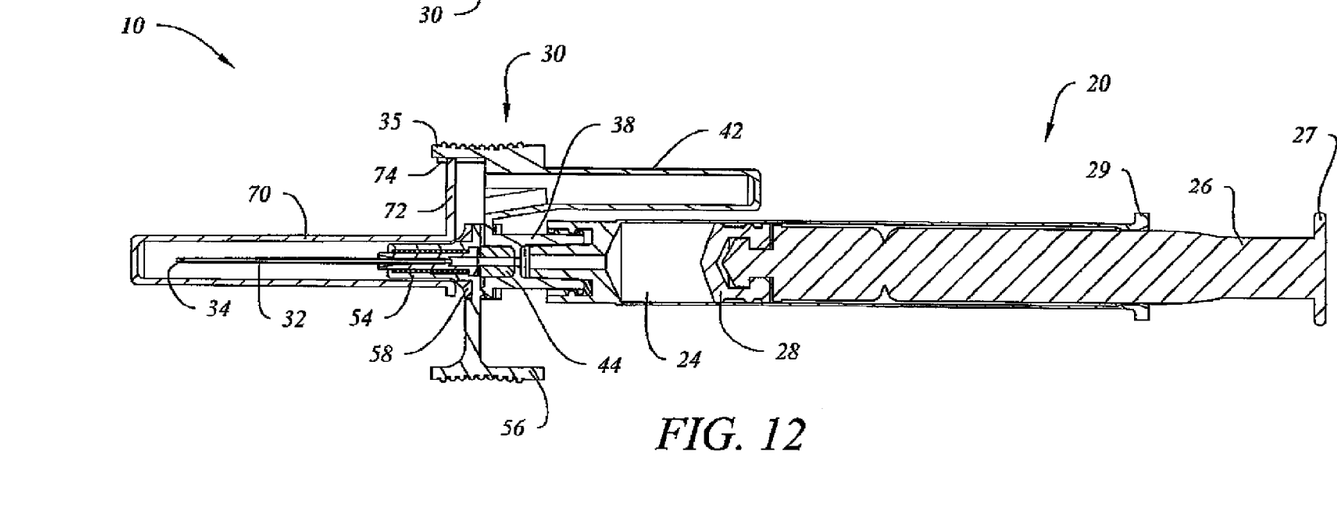
FIG. 12 is a cross-sectional view of the device of FIG. 1.

FIGS. 11 and 12 illustrate elevation and rotated cross-sectional views of the assembled device as in FIG. 1, but with a needle cap 70 installed to protect the needle from damage or Contamination prior to use of the device. In FIG. 12, a laterally projecting tab 72, 74 is visible that engages the inwardly facing side of pinch tab 56 to restrict relative movement and premature needle retraction while needle cap 70 is in place.

Syringe engaging member 36, needle holder 46, needle alignment member 52, syringe barrel 20 and plunger handle 26 are all desirably moldable from a suitable moldable polymeric material. Such materials and molding methods are believed to be well known to those of ordinary skill in the art. Similarly, it will be appreciated by those of skill in the art of syringe design and manufacture that a medical device such as retractable needle device 30 disclosed here can be used with syringes that are either pre-filled or not, and that can comprise component portions made of glass or other suitable materials for particular applications. Similarly, it will be appreciated that fluid seal 44 and plunger seal 28 are desirably made of a rubbery or elastomeric polymeric material of the types commonly known for use in such medical applications. Similarly, it will be appreciated that materials used in the fabrication of this and other medical devices must be approved by the relevant regulatory authorities for use in such devices. Needle 32 as disclosed is desirably made of stainless steel and retraction spring 44 can be made of stainless steel or any other similarly effective medical grade material.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

The invention claimed is:

1. A retractable needle device selectively attachable to a fluid collection or infusion device having a forwardly facing connector, the retractable needle device comprising:
    a housing further comprising a forwardly facing slide support surface and a first pinch tab;
    a needle alignment member further comprising a forwardly projecting needle tube, a rearwardly facing surface that slidably engages the forwardly facing slide support surface, and a second pinch tab;
    a retractable needle projecting forwardly of the needle alignment member prior to use of the device;
    a needle retraction mechanism seated inside the needle tube; and
    a retainer clip comprising a hole configured to engage the needle tube and retaining brackets configured to retain the needle alignment member against the housing;
    wherein the first pinch tab and the second pinch tab are cooperatively configured so that a pinching force applied to the first pinch tab and to the second pinch tab perpendicularly to a longitudinal axis through the needle causes the housing to move transversely from a first position to a second position to initiate needle retraction.

2. The retractable needle device of claim 1 wherein the housing further comprises a connector tube and a retraction tube.

3. The retractable needle device of claim 1 wherein the needle retraction mechanism comprises a retraction spring.

* * * * *